(12) United States Patent
Ravikumar et al.

(10) Patent No.: US 10,722,297 B2
(45) Date of Patent: *Jul. 28, 2020

(54) MINIMALLY INVASIVE SURGICAL NEEDLE AND CAUTERIZING ASSEMBLY AND METHODS

(71) Applicant: TELEFLEX MEDICAL INCORPORATED, Research Triangle Park, NC (US)

(72) Inventors: Sundaram Ravikumar, Briarcliff Manor, NY (US); H. Allan Alward, Shelton, CT (US); Robert F. Smith, Jr., Waterbury, CT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 858 days.

This patent is subject to a terminal disclaimer.

(21) Appl. No.: 14/605,614

(22) Filed: Jan. 26, 2015

(65) Prior Publication Data

US 2015/0148800 A1   May 28, 2015

Related U.S. Application Data

(63) Continuation of application No. 12/100,185, filed on Apr. 9, 2008, now Pat. No. 8,956,351.

(51) Int. Cl.
*A61B 18/14* (2006.01)
*A61B 17/00* (2006.01)
*A61B 18/00* (2006.01)

(52) U.S. Cl.
CPC .............. *A61B 18/1477* (2013.01); *A61B 2017/00349* (2013.01); *A61B 2017/00973* (2013.01);
(Continued)

(58) Field of Classification Search
CPC ........ A61B 2018/1475; A61B 2018/12; A61B 2018/1405; A61B 2018/00327;
(Continued)

(56) References Cited

U.S. PATENT DOCUMENTS 3,817,251 A   6/1974   Hasson
3,844,291 A   10/1974  Moen
(Continued)

OTHER PUBLICATIONS

"Cauterization", Wikipedia entry, Mar. 14, 2008, 4 pages.

*Primary Examiner* — Jaymi E Della
(74) *Attorney, Agent, or Firm* — Baker & Hostetler LLP

(57) ABSTRACT

A minimally invasive surgical assembly broadly includes an outer hollow needle which has an outer diameter, a longitudinal axis, and a sharp distal end. An insulating member extends through the hollow needle and is movable relative to the hollow needle. An elongated member extends through the insulating member and is movable relative to both the insulating member and the hollow needle. A resilient wire projects from the elongated member and is retractable within and extendable outside of the insulating member and the hollow needle. The insulating member, elongated member, and resilient wire are movable relative to the needle using first and second moving means whereby the surgical assembly assumes various configurations having different operational functions.

19 Claims, 7 Drawing Sheets

(52) U.S. Cl.
CPC ............... *A61B 2018/00595* (2013.01); *A61B 2018/144* (2013.01); *A61B 2018/1475* (2013.01)

(58) Field of Classification Search
CPC .......... A61B 2018/00333; A61B 2018/00339; A61B 2018/00357; A61B 2018/00363; A61B 2018/00488; A61B 2018/00494; A61B 2018/00511; A61B 2018/00547; A61B 2018/00553
See application file for complete search history.

(56) References Cited

U.S. PATENT DOCUMENTS

| | | | |
|---|---|---|---|
| 3,906,955 A | 9/1975 | Roberts | |
| 3,938,527 A | 2/1976 | Rioux et al. | |
| 3,955,578 A * | 5/1976 | Chamness | A61B 17/32056 606/47 |
| 4,016,881 A | 4/1977 | Rioux et al. | |
| 4,077,412 A | 3/1978 | Moosun | |
| 4,174,715 A | 11/1979 | Hasson | |
| 4,570,642 A | 2/1986 | Kane et al. | |
| 4,657,018 A | 4/1987 | Hakky | |
| 4,688,569 A * | 8/1987 | Rabinowitz | A61B 18/1402 606/37 |
| 4,711,238 A * | 12/1987 | Cunningham | A61B 18/14 606/79 |
| 4,869,248 A | 9/1989 | Narula | |
| 5,073,169 A | 12/1991 | Raiken | |
| 5,100,402 A | 3/1992 | Fan | |
| 5,147,316 A | 9/1992 | Castillenti | |
| 5,176,643 A | 1/1993 | Kramer et al. | |
| 5,176,697 A | 1/1993 | Hasson et al. | |
| 5,201,741 A | 4/1993 | Dulebohn | |
| 5,201,742 A | 4/1993 | Hasson | |
| 5,222,973 A | 6/1993 | Sharpe et al. | |
| 5,224,954 A | 7/1993 | Watts et al. | |
| 5,290,276 A | 3/1994 | Sewell, Jr. | |
| 5,330,497 A | 7/1994 | Freitas et al. | |
| 5,342,357 A | 8/1994 | Nardella | |
| 5,354,283 A | 10/1994 | Bark et al. | |
| 5,375,588 A | 12/1994 | Yoon | |
| 5,417,697 A | 5/1995 | Wilk et al. | |
| 5,486,161 A * | 1/1996 | Lax | A61B 10/0233 604/22 |
| 5,496,314 A * | 3/1996 | Eggers | A61B 18/082 606/29 |
| 5,556,411 A | 9/1996 | Taoda et al. | |
| 5,578,030 A | 11/1996 | Levin | |
| 5,626,597 A | 5/1997 | Urban et al. | |
| 5,634,918 A | 6/1997 | Richards | |
| 5,658,272 A | 8/1997 | Hasson | |
| 5,672,173 A | 9/1997 | Gough et al. | |
| 5,800,378 A | 9/1998 | Edwards et al. | |
| 5,857,999 A | 1/1999 | Quick et al. | |
| 5,871,453 A | 2/1999 | Banik et al. | |
| 5,893,873 A | 4/1999 | Rader et al. | |
| 5,906,620 A | 5/1999 | Nakao et al. | |
| 5,951,488 A | 9/1999 | Slater et al. | |
| 5,964,756 A | 10/1999 | McGaffigan et al. | |
| D426,883 S | 6/2000 | Berman et al. | |
| 6,099,550 A | 8/2000 | Yoon | |
| 6,391,046 B1 | 5/2002 | Overaker et al. | |
| 6,428,503 B1 | 8/2002 | Kierce | |
| 6,616,683 B1 | 9/2003 | Toth et al. | |
| 6,630,103 B2 | 10/2003 | Martin et al. | |
| 6,648,839 B2 | 11/2003 | Manna et al. | |
| 6,736,814 B2 | 5/2004 | Manna et al. | |
| 6,761,718 B2 | 7/2004 | Madsen | |
| 6,860,894 B1 | 3/2005 | Pittman | |
| 6,902,536 B2 | 6/2005 | Manna et al. | |
| 6,908,454 B2 | 6/2005 | McFarlane | |
| 6,945,984 B2 | 9/2005 | Arumi et al. | |
| 7,001,333 B2 | 2/2006 | Hamel et al. | |
| 7,150,747 B1 * | 12/2006 | McDonald | A61B 18/148 606/45 |
| 7,223,267 B2 | 5/2007 | Isola et al. | |
| 2001/0056286 A1 | 12/2001 | Etter et al. | |
| 2003/0040773 A1 | 2/2003 | Arumi et al. | |
| 2003/0130693 A1 | 7/2003 | Levin et al. | |
| 2003/0145865 A1 | 8/2003 | Sterman et al. | |
| 2004/0225286 A1 | 11/2004 | Elliott | |
| 2005/0113737 A1 | 5/2005 | Ashby et al. | |
| 2005/0273133 A1 | 12/2005 | Shulzas et al. | |
| 2006/0079883 A1 * | 4/2006 | Elmouelhi | A61B 18/1492 606/41 |

* cited by examiner

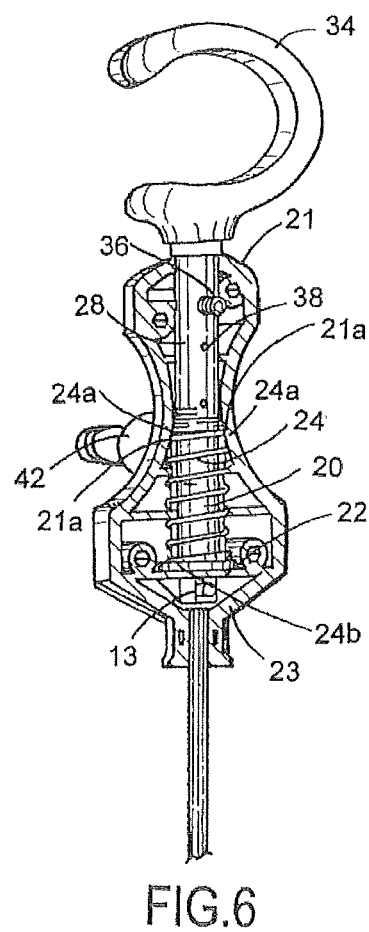
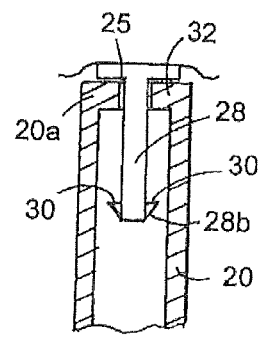
FIG.6
FIG.7

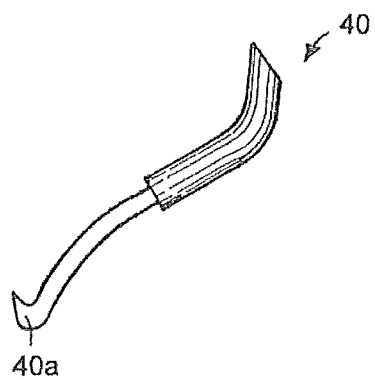
FIG.8
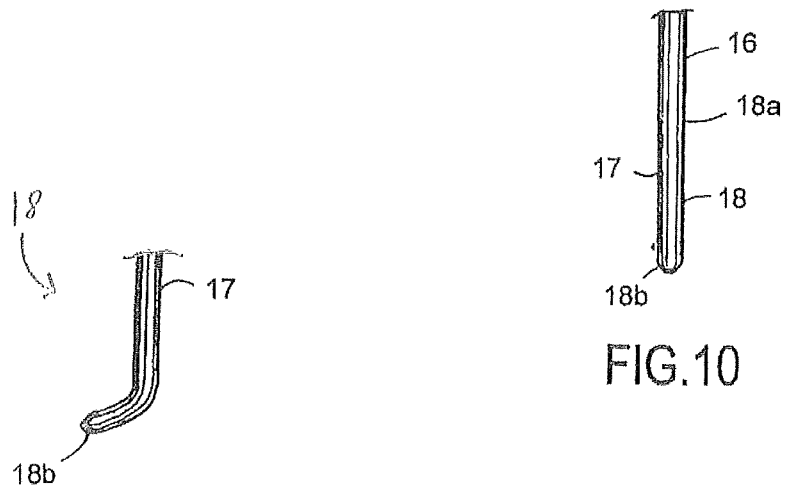
FIG.9
FIG.10

MINIMALLY INVASIVE SURGICAL NEEDLE AND CAUTERIZING ASSEMBLY AND METHODS

CROSS-REFERENCE TO RELATED APPLICATIONS

This application is a continuation application of U.S. patent application Ser. No. 12/100,185, filed on Apr. 9, 2008, the disclosure of each of which is incorporated by reference in its entirety.

BACKGROUND OF THE INVENTION

1. Field of the Invention

This invention relates broadly to surgical instruments and methods of their use. More particularly, this invention relates to a minimally invasive surgical assembly that incorporates both a needle and a cauterizing device that is extendible through and beyond the needle and retractable into the needle. The invention has particular application to laparoscopic-type surgery, although it is not limited thereto.

2. State of the Art

Over the last two decades, minimally invasive surgery has become the standard for many types of surgeries which were previously accomplished through open surgery. Minimally invasive surgery generally involves introducing an optical element (e.g., laparoscope or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly. The trocar assembly often includes a port, a sharp pointed element (trocar) extending through and beyond the distal end of the port, and at least in the case of abdominal laparoscopy, a valve on the proximal portion of the port. Typically, a small incision is made in the skin at a desired location in the patient. The trocar assembly, with the trocar extending out of the port, is then forced through the incision, thereby widening the incision and permitting the port to extend through the incision, past any facie, and into the body (cavity). The trocar is then withdrawn, leaving the port in place. In certain circumstances, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include 5 mm, 10 mm and 12 mm (available from companies such as Taut and U.S. Surgical), which are sized to permit variously sized laparoscopic instruments to be introduced therethrough including, e.g., graspers, dissectors, staplers, scissors, suction/irrigators, clamps, forceps, biopsy forceps, etc. Laparoscopic surgery has reduced the trauma associated with various surgical procedures and has concomitantly reduced recovery time from these surgeries. The 5 mm trocar ports from the various instruments used in laparoscopic surgery leave a plurality of holes that must be stitched, which typically result in scars.

One surgical instrument often used during laparoscopic surgery is a cauterization tool. Cauterization (cautery) tools are employed for stopping internal bleeding by cauterizing areas inside the body that have been pierced or opened during surgery, and for cutting through tissue inside of the body in order to destroy and/or remove it. The cautery tool is typically electrified to destroy the tissue. The cautery device may be electrified at different voltages to achieve different functions. At lower voltages, continuous alternating current quickly produces heat that vaporizes tissue at the tip of the cautery tool. At higher voltages, heat is produced more slowly, which causes more widespread tissue damage near the tip of the cautery tool. The latter effect causes blood near the site to coagulate. The process of using electricity to destroy tissue is called "electrocauterization."

Electrocauterization is performed in either a monopolar or bipolar mode. In monopolar electrocauterization, a patient's body serves as the ground, and current passes from the cautery device to the patient. In bipolar electrocauterization, the cautery device contains sending and receiving electrodes that are placed around tissue. The current passes between the electrodes and cauterizes the tissue therebetween.

A common cautery device used in monopolar electrocauterization is a scalpel-shaped spatula, which may serve as both a coagulator and an electric scalpel. A surgeon operates the cautery device by pushing a button on its shaft and/or by depressing a foot pedal, thereby allowing current to flow through the cautery device.

A number of cautery and needle combinations are known in the art. U.S. Pat. No. 5,578,030 discloses a biopsy needle that procures a tissue specimen and cauterizes the resulting wound, which minimizes bleeding and helps prevent the proliferation of cancer cells along the path of the needle. The device has a sharp cutting edge disposed at a junction between a front wall and a top surface, a configuration that enables tissue to be cut and forced into the biopsy needle as the biopsy needle is retracted from a patient. A conductor applies electrical current to the needle, which heats it and cauterizes the wound resulting from the excision of the tissue specimen.

U.S. Pat. No. 5,342,357 discloses an electrosurgical probe that cuts and cauterizes tissue. The device is adapted to accommodate fluid flow through an outlet port to surrounding tissue so as to limit heat transfer from the device thereto, thereby preventing the surrounding tissue from sticking to the device.

U.S. Pat. No. 5,906,620 discloses a surgical instrument assembly that includes a cauterization snare and a suture member, both of which are disposed in a first tubular sheath. The suture member is also disposed in a second tubular sheath that facilitates the release and positioning of the suture member around a selected body of tissue. The second tubular sheath is movably disposed in the first tubular sheath and contains a tensioning means extending through the second tubular sheath for tightening the suture member. The device is used to remove a polyp or other body tissue.

SUMMARY OF THE INVENTION

A minimally invasive surgical assembly is provided. The surgical assembly according to the invention broadly includes an outer hollow needle having a longitudinal axis and a sharp distal end for piercing tissue, an insulating member extending coaxially through and movable relative to the hollow needle, an elongated member extending coaxially through and movable relative to the insulating member and the hollow needle, a resilient wire attached to and projecting outward from a distal end of the elongated member to a cauterization tip, and a proximal assembly for moving the insulating and elongated members to various positions relative to the needle and to each other. A housing mounted to the outer surface of the needle encapsulates and protects the proximal assembly, functions as a secondary handle or grip for an operator holding the surgical assembly, and preferably provides air tight seals at the proximal end of the needle while allowing the insulating and elongated members, which extend into the housing, to move relative thereto. By moving the insulating and elongated members relative to each other and relative to the needle, various configurations are obtained, each of which has its own benefits and/or operational functions.

In the preferred embodiment, the proximal assembly includes a first mechanism for causing the elongated member to move relative to both the needle and the insulating member, and a second mechanism for moving the insulating member relative to the needle. The first mechanism of the proximal assembly is a plunger and a handle or finger loop. The plunger on one end is mounted to the proximal end of the elongated member and on the other is affixed to the handle. The plunger is movable along the longitudinal axis of the needle and drives the elongated member and the resilient wire to various positions relative to the sharp distal end of the needle.

The second mechanism of the proximal assembly includes a cage mounted to the proximal end of the insulating member, and a spring mounted at a proximal end to a portion of the housing. The spring preferably wraps around the cage and biases the cage toward a distal position. Proximal movement of the cage and attached insulating member is achieved when the plunger engages the cage and is moved in a proximal direction. Distal movement of the cage and attached insulating member is achieved by the bias of the spring when the plunger is moved in a distal direction. The housing of the surgical assembly limits the distal displacement of the cage. Thus, the bias of the spring moves the cage in a distal direction as the plunger is moved in a distal direction until the cage is stopped by the housing. At that point, the plunger decouples from the cage and is further movable in a distal direction. These first and second mechanisms allow the surgical assembly to achieve various functional configurations from a relatively simple linear motion of the plunger.

In the preferred embodiment, the surgical assembly includes a fixing means for fixing the surgical assembly in first, second, third, and fourth configurations. In the first configuration, the distal end of the insulating member and the cauterizing tip of the resilient wire are disposed inside the needle such that the sharp distal end of the needle is exposed and ready for insertion into a patient. In the second configuration, the distal end of the insulating member is disposed beyond the sharp distal end of the needle, which protects and insulates the sharp distal end, and the cauterizing tip of the resilient wire is disposed inside the insulating member, which electrically insulates the cauterizing tip and allows the surgical assembly to be maneuvered within the patient without cutting or cauterizing any tissue. In the third configuration, the distal end of the insulating member is disposed beyond the sharp distal end of the needle, and the cauterizing tip is disposed just beyond the distal end of the insulating member. This configuration allows for electrical activation and operation of the cauterizing tip while insulating the sharp distal end of the needle. In the fourth configuration, the distal end of the insulating member is disposed beyond the sharp distal end of the needle, and the resilient wire is fully extended and bent such that the cauterization tip is offset from the longitudinal axis of the needle by a distance at least as large as one half of the outer diameter of the needle, and preferably by a distance exceeding twice the diameter of the needle. This configuration allows for electrical activation and operation of the cauterizing tip at a location outside of the cylindrical projection of the hollow needle, thereby increasing the area within the patient that a surgeon can reach after inserting the surgical assembly at a specific location through a small incision.

The surgical assembly may be used during laparoscopic surgery instead of using an extra trocar and laparoscopic instrument. In particular, with the insulating member, the elongated member, and the attached resilient wire with the cauterization tip all disposed inside the needle, the needle is used to puncture the skin, and is advanced into the body (e.g., the abdomen). At a desired location (typically under guidance of an already inserted scope), the movement of the needle is stopped. The plunger is then distally advanced relative to the needle, which distally advances the insulating member relative to the needle until the distal end of the insulating member extends past the sharp distal end of the needle. This configuration insulates the needle and acts as a barrier to prevent injury or trauma to the patient in the event that the needle is inadvertently further inserted. With the needle now in a relatively fixed position, the plunger is further distally advanced relative to the needle, which distally advances the elongated member and resilient wire relative to both the needle and the insulating member. In a first distal position, the cauterizing tip of the resilient wire extends just beyond the distal end of the insulating member, is in-line with the longitudinal axis of the needle, and may be used as a cautery device in that capacity. As the elongated member is moved further distally beyond the first distal position, the cauterizing tip of the resilient wire, as it is advanced beyond the distal ends of the needle and insulating member, automatically moves transverse to the longitudinal axis of the needle. In a second distal (fully extended) position, the bias of the resilient wire toward the bent configuration has caused the resilient wire to bend enough to dispose the cauterizing tip of the resilient wire at an offset location relative to the longitudinal axis of the needle.

Preferably, the cauterizing tip of the resilient wire is electrified once it extends beyond the distal ends of the insulating member and needle. The surgical assembly may then be used as a cauterizing device. At any time, the resilient wire and elongated member may be retracted within the needle by proximally moving the plunger relative to the needle. The surgical assembly can then be pulled out of the body, leaving only a small puncture mark which will often heal without stitching and a scar.

Objects and advantages of the invention will become apparent to those skilled in the art upon reference to the detailed description taken in conjunction with the provided figures.

BRIEF DESCRIPTION OF THE DRAWINGS

FIG. 6 is the view of FIG. 4 with the plunger of the surgical assembly in place.

FIG. 7 is a broken cross sectional view of the plunger and cage of the surgical assembly in the configuration of FIG. 3D.

FIG. 8 is an enlarged view of the electrical clip of the surgical assembly of FIG. 4.

FIG. 9 is an enlarged side perspective view of the resilient wire of the surgical assembly of FIG. 1.

FIG. 10 is an enlarged front perspective view of the resilient wire of the surgical assembly of FIG. 1.

DETAILED DESCRIPTION OF THE PREFERRED EMBODIMENTS

Figure 1:
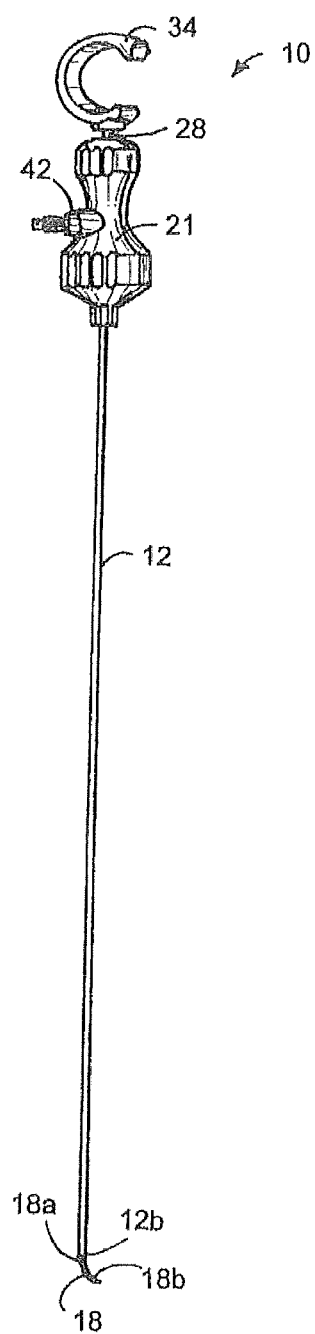
FIG. 1 is perspective view of a preferred embodiment of the surgical assembly of the invention with the cauterizing tip of the surgical instrument in an extended position.

A minimally invasive surgical assembly 10 according to the invention and as seen in FIGS. 1-5 broadly includes an outer hollow needle 12, an insulating member 14 extending coaxially through the needle 12, an elongated member 16 (FIGS. 2D, 4) extending coaxially through the insulating member 14 and the needle 12 which terminates in a resilient wire 18, and a proximal assembly 19 for coaxially moving the insulating and elongated members 14, 16 to various positions relative to the needle 12 and to each other. A housing 21 mounted to the outer surface of the needle 12 encapsulates and protects the proximal assembly 19, functions as a secondary handle or grip for an operator holding the surgical assembly 10, and accommodates the relative movement of the insulating member 14 and elongated member 16 relative to the needle 12 and to each other while preferably maintaining a sealed, air tight environment. Various configurations of the surgical assembly 10, each having different benefits and/or functional operations, are achieved by moving the insulating and elongated members 14, 16 relative to the needle 12 and to each other as described hereinafter.

The needle 12 has a proximal end 12a (FIG. 4), a sharp distal end 12b, and a longitudinal axis 12c (FIGS. 2A-2D). The preferred needle 12 of the invention has an outer diameter of 2.2 mm (0.087 inches).+−0.20% and is angled at the sharp distal end 12b at about 35.degree. relative to the longitudinal axis 12c of the needle 12 for piercing through tissue. The needle 12 preferably has an inside diameter of 1.7 mm (0.067 inches), a wall thickness of 0.25 mm (0.01 inch), is typically between 10 and 30 cm long, and more typically between 13 and 18 cm long (although other sizes could be used, depending upon the surgery involved, and typically larger for obese patients and smaller for infants and small children), and is preferably made from stainless steel, although other materials could be utilized. The needle 12 preferably has an outer layer of insulation 15 (FIGS. 2A-2D). Insulation 15 is preferably a shrink wrap layer having a very high dielectric strength, e.g., greater than 4,000 V/mil, which prevents electrical discharge passing through the needle 12 and insulates the needle 12 from being charged when the surgical assembly 10 is used as a cauterization device as further discussed below.

The insulating member 14 of the surgical assembly 10 has a proximal end 14a (FIGS. 3A-3D) and a distal end 14b (FIGS. 2B-2D), extends coaxially through the needle 12, and is movable relative thereto. The insulating member 14 is preferably made from material such as polyimide tubing having a very high dielectric strength, e.g., greater than 4,000 V/mil. Insulating member 14 preferably has a wall thickness of at least 0.001 inches, and more preferably is approximately 0.005-0.012 inches thick, and most preferably 0.009 inches thick. Insulating member 14 has an outer diameter of approximately 0.065 inches.

The elongated member 16 has a proximal end 16a (FIG. 4), a distal end 16b (FIG. 2D), extends coaxially through the insulating member 14 and the needle 12, and is movable relative to both the insulating member 14 and the needle 12. The elongated member 16 is preferably formed from stainless steel in the shape of an elongated rod, although other materials and shapes could be utilized. The elongated member 16 is preferably about 0.03-0.04 inches in diameter.

Figure 2A:
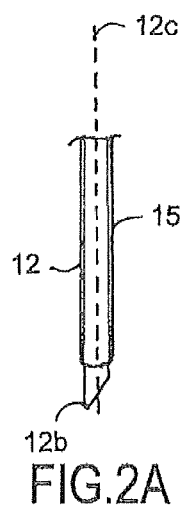
FIG. 2A is a broken perspective view of the distal end of the needle of the surgical assembly of FIG. 1 in a first configuration.
Figure 2B:
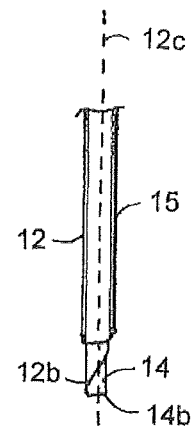
FIG. 2B is a broken perspective view of the distal end of the needle and insulating member of the surgical assembly of FIG. 1 in a second configuration.
Figure 2C:
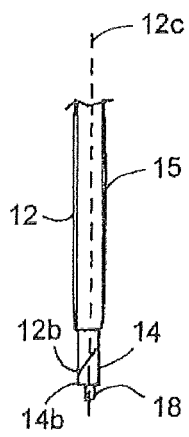
FIG. 2C is a broken perspective view of the distal end of the needle, insulating member, and resilient wire of the surgical assembly of FIG. 1 in a third configuration.
Figure 2D:
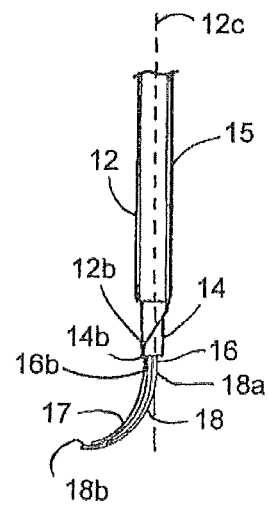
FIG. 2D is a broken perspective view of the distal end of the needle, insulating member, elongated member, and resilient wire of the surgical assembly of FIG. 1 in a fourth configuration.

As seen in FIG. 2D, the resilient wire 18 has a proximal end 18a and a distal cauterizing tip 18b. The resilient wire 18 is preferably made from 17-7 heat treated stainless steel, is 0.012 inches thick, 1.2 inches long, 0.045 inches wide, and effectively presents as a flat curved spatula (FIG. 10). The flattened resilient wire 18 is retractable within both the insulating member 14 and the hollow needle 12, and the cauterizing tip 18b of the resilient wire 18 is extendable beyond distal ends 12b, 14b, of the hollow needle 12 and the insulating member 14. The resilient wire 18 is biased toward a bent configuration (as shown in FIGS. 1, 2D, and 9) such that, when extended beyond the distal ends 12b, 14b of the hollow needle 12 and the insulating member 14, the cauterizing tip 18b automatically bends relative to the longitudinal axis 12c of the hollow needle 18. The proximal end 18a of the resilient wire 18 may be welded to the distal end 16b of the elongated member 16, or attached to the elongated member 16 in any other desired manner known in the art. All but the distal ¼ inch of the resilient wire 18 is coated with an insulation 17 (FIGS. 2D, 9). As further discussed below, the resilient wire 18 of the surgical assembly 10 operates as an extendable and retractable cauterization tool within the hollow needle 10, and the relative locations of the needle 12, insulating member 15, elongated member 16, and resilient wire 18 give various functional benefits to the surgical assembly 10.

The housing 21 is mounted to the outer surface of the needle 12 and encapsulates and protects the proximal assembly 19. The housing 21 is preferably similar to the proximal housing that is described in commonly owned U.S. patent application Ser. No. 11/685,522 (referred to therein as the handle 520), which is herein incorporated by reference in its entirety. The needle 12 has a hub 13 (FIGS. 3A-3D) which is trapped in a distal portion 23 (FIGS. 3A-3D, 4, and 6) of the housing 21. The housing 21 should be made from a non-electrically conducting material such as plastic.

Figure 3A:
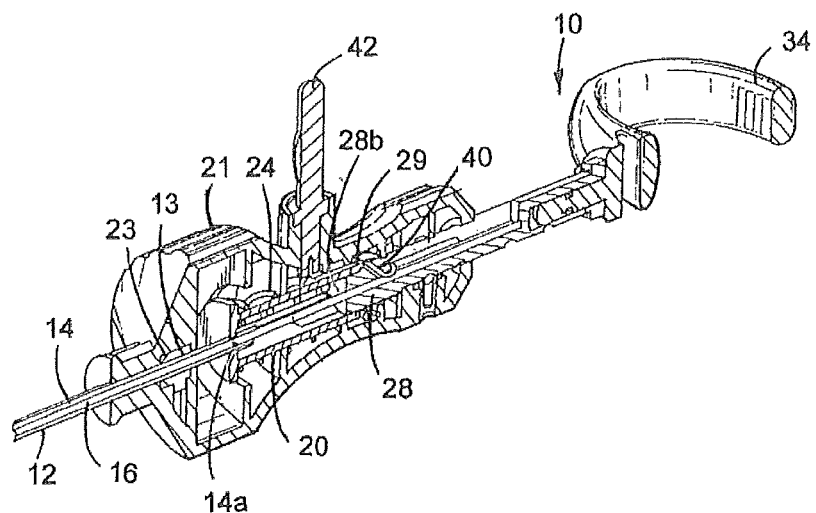
FIG. 3A is a broken longitudinal sectional view of the surgical assembly of FIG. 1 in a first configuration.
Figure 3B:
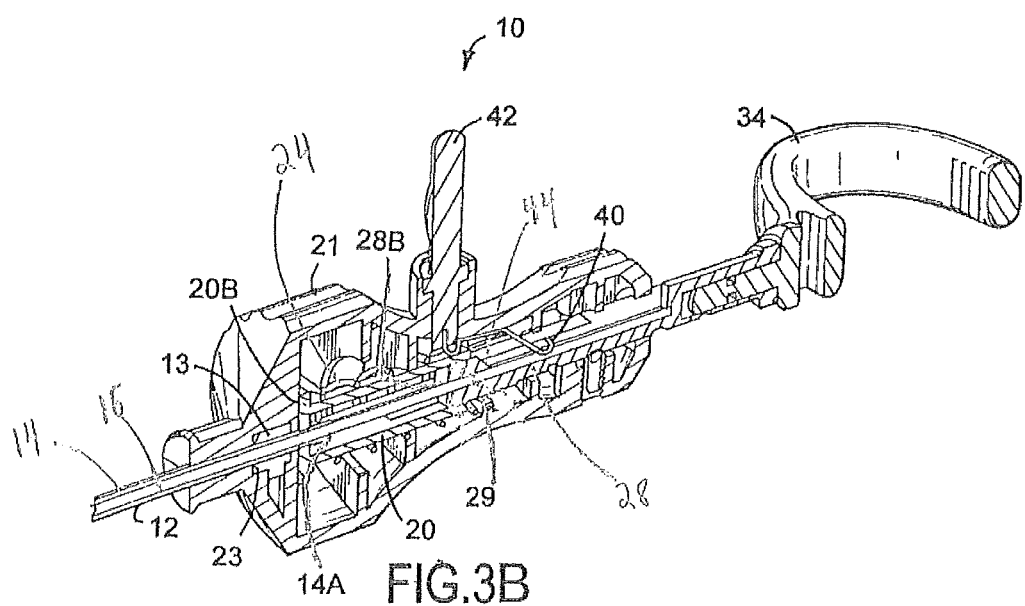
FIG. 3B is a broken longitudinal sectional view of the surgical assembly of FIG. 1 in a second configuration.
Figure 3C:
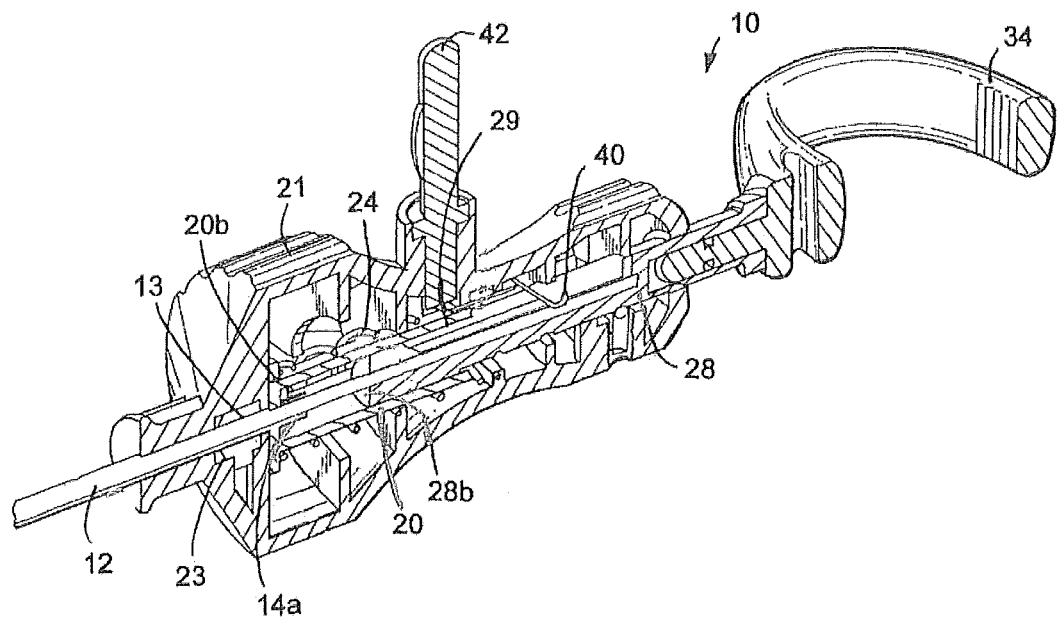
FIG. 3C is a broken longitudinal sectional view of the surgical assembly of FIG. 1 in a third configuration.
Figure 3D:
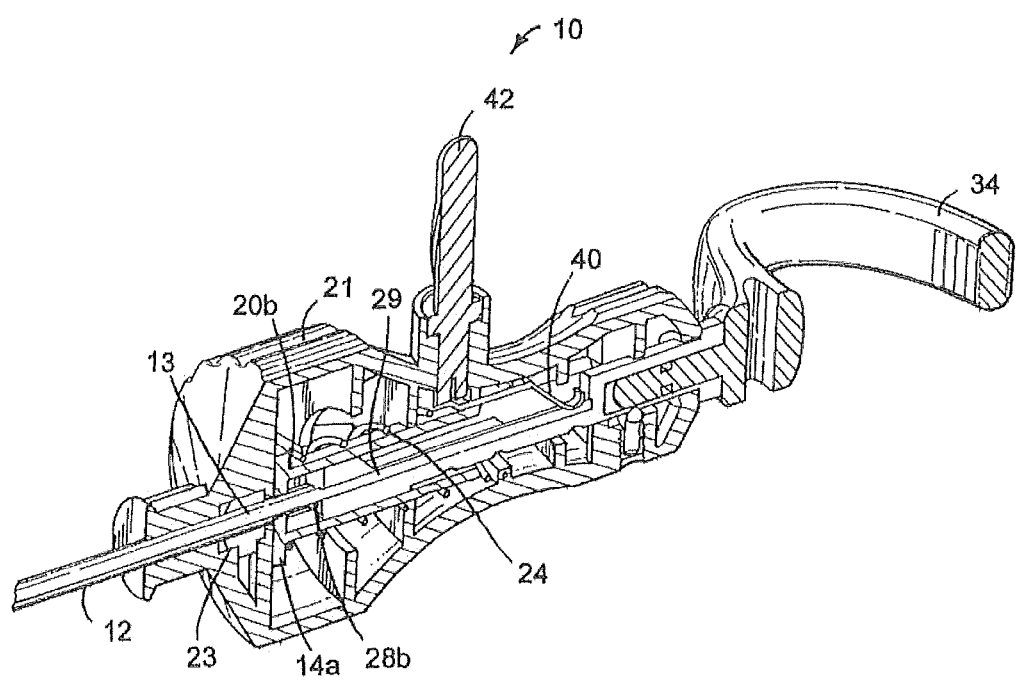
FIG. 3D is a broken longitudinal sectional view of the surgical assembly of FIG. 1 in a fourth configuration.
Figures 4, 5:
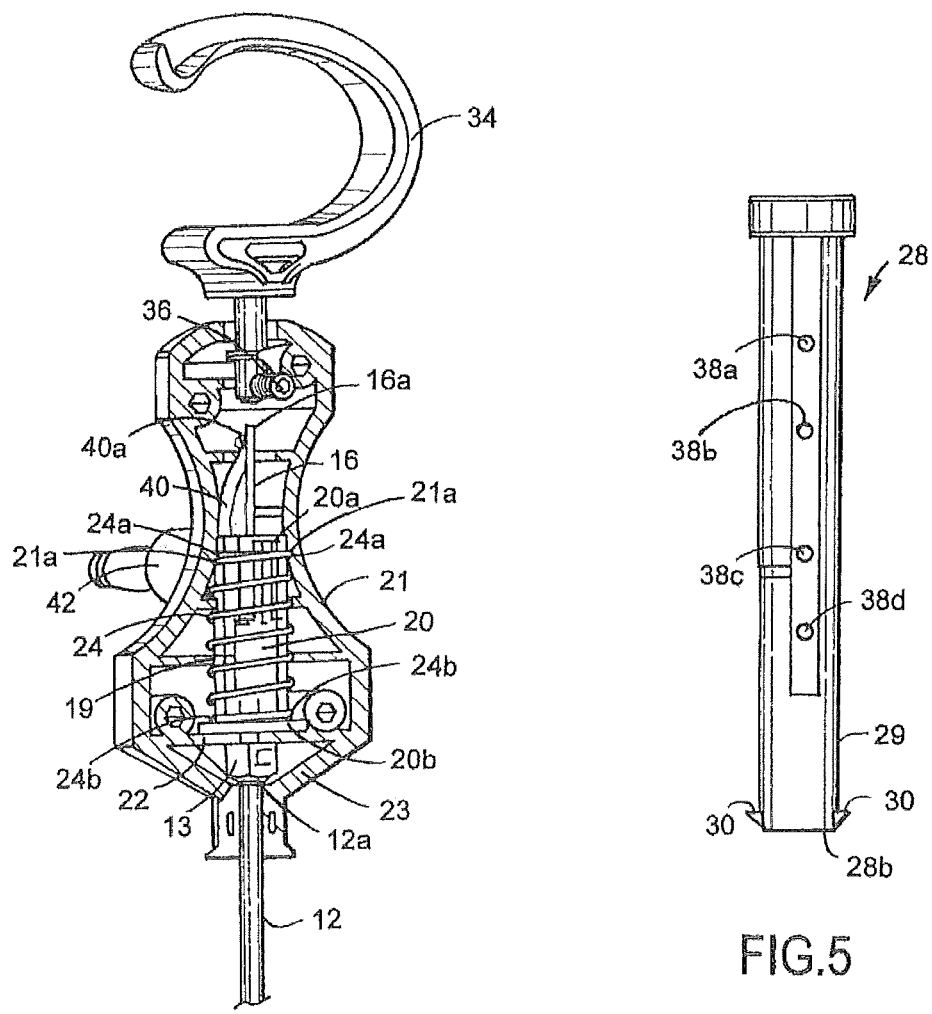
FIG. 4 is a broken partial cutaway perspective view of the proximal end of the surgical assembly in the configuration of FIG. 3D with the plunger removed.
FIG. 5 is an enlarged view of the plunger of the surgical assembly of FIGS. 3A-3D.

Turning to FIGS. 4 and 6, the proximal assembly 19 includes mechanisms capable of moving the insulating and elongated members 14, 16 to various positions relative to the needle 12 and relative to each other, including moving the insulating member 14 relative to the needle 12, and moving the elongated member 16 relative to both the needle 12 and the insulating member 14. In the preferred embodiment, as shown in FIGS. 4-7, one mechanism includes a cage 20 having a proximal end 20a, a distal end flange 20b, and a spring 24. The spring 24 has a proximal end 24a fixed to the housing 21 and a distal end 24b resting on or mounted to the distal end flange 20b of the cage 20. The fixed proximal end 24a of the spring 24 is preferably fixed within notches or recesses 21a (FIGS. 4, 6) defined by the housing 21. The distal end flange 20b of the cage 20 is preferably disk shaped and wide enough to act as a base against which the distal end 24b of the spring 24 abuts (See FIGS. 3B-3D). In the configuration of the surgical assembly 10 shown in FIGS. 4 and 6, which is further discussed below, the distal end flange 20b of the cage 20 is in contact with a horizontal member 22 of the housing 21.

The cage 20 is mounted to the proximal end 14a of the insulating member 14. The mounting can be accomplished by adhering with adhesive the proximal end 14a of the insulating member 14 to the circumference of a central hole (not shown) defined in the distal end flange 20b of the cage 20. Alternatively, the insulating member 14 and cage 20 may be affixed together mechanically. The cage 20 is movable to upper (FIG. 3A) and lower positions (FIGS. 3B-3D) relative to the housing 21 and needle 12. When the cage 20 is in the lower position, the flange portion 20b is in direct contact with the horizontal member 22 of the housing 21. The horizontal member 22 defines a hole through which the insulating member 14 extends, and prevents the cage 20 from moving distally beyond the lower position toward the sharp distal end 12b of the needle 12. The spring 24 preferably wraps around the cage 20 and extends downward from the fixed proximal end 24a to the movable distal end 24b, which moves with the cage 20 along the longitudinal axis 12c of the needle 12. As the cage 20 is moved toward the upper position (FIG. 3A), the movable distal end 24b of the spring 24 is pushed upward by the distal end 20b of the cage 20, which compresses the spring 24. The spring 24 thus biases the cage 20 toward the lower position (FIGS. 3B-3D, 4) absent any counter acting forces on the cage 20.

The cage 20, spring 24, and insulating member 14 are operably situated and dimensioned such that when the cage 20 is in the upper position (FIG. 3A), the distal end 14b of the insulating member 14 is disposed inside of the hollow needle 12, and the sharp distal end 12b of the needle 12 is exposed (FIG. 2A). As the cage 20 moves distally toward the lower position (FIGS. 3B-3D), the insulating member 14, whose proximal end 14a is mounted to the cage 20, is moved distally relative to the hollow needle 12, whereby the distal end 14b of the insulating member 14 may be moved beyond the sharp distal end 12b of the needle 12 in order to protect and insulate the sharp distal end 12b (FIGS. 2B-2D).

In the preferred embodiment, the proximal assembly 19 also includes a plunger 28 mechanically coupled to the proximal end 16a (FIG. 4) of the elongated member 16. The plunger 28 is connected to a handle 34 that may be grasped by a user in order to proximally and distally move the plunger 28. The handle 34 connected to the plunger 28 is preferably identical or similar to that described in commonly owned U.S. patent application Ser. No. 11/685,522. The plunger 28 is longitudinally movable to proximal, intermediate, and distal positions relative to the housing 21 as described hereinafter.

As shown in FIGS. 5 and 7, the plunger 28 preferably has projections, hooks, or a flange 30 projecting from a distal end 28b of the plunger 28. As the plunger 28 is moved proximally (away from the distal end 12b of the needle 12) the hooks 30 of the plunger 28 couple with the cage 20 and pull the cage 20 toward the upper position. In the preferred embodiment shown, the cage 20 is hollow so that the plunger 28 is coaxially movable inside the cage 20. Thus, as shown in FIG. 7, the cage 20 may be formed with a small opening 25 at or near its proximal end 20a such that when the hooks 30 of the plunger 28 reach the opening 25, they cannot fit therethrough. The hooks 30 therefore grab onto the rim 32 formed inside the cage 20 whereby the cage 20 is pulled by the plunger 28 in a proximal direction relative to the needle 12. As the cage 20 moves toward the upper position (FIG. 3A), the movable distal end 24b of the spring 24, which is either mechanically coupled to or resting on top of the horizontal distal portion 20b of the cage 20, moves with the cage 20, thus compressing the spring 24 between the fixed proximal end 24a and the movable distal end 24b.

The surgical assembly 10 preferably includes a mechanism for fixing the surgical assembly 10 in first, second, third, and fourth configurations (shown in FIGS. 3A-3D, which correspond to FIGS. 2A-2D). The mechanism for fixing the surgical assembly 10 in one of the four configurations includes a spring-loaded ball set screw 36 (FIGS. 4 and 6) that is mounted in the housing 21. The set screw 36 is received by holes or detents 38a, 38b, 38c, and 38d (FIG. 5) defined by the plunger 28 as the plunger 28 is moved proximally and distally within the needle 12, which temporarily locks the surgical assembly 10 into one of the configurations. The plunger 28 is moved out of a given configuration by pushing or pulling the plunger 28 distally or proximally, thereby applying enough force to the plunger 28 to overcome the temporary lock created by the set screw 36 and a given hole or detent 38a-d.

In the first configuration (FIGS. 2A, 3A), the surgical assembly 10 is in an armed retracted position with the sharp distal end 12b of the needle exposed. In this configuration, the handle 34 and plunger 28 are disposed in the most proximal position, and the cage 20 is in the upper (most proximal) position, which positions the distal end 14b of the insulating member 14 inside the needle 12 such that the sharp distal end 12b of the needle 12 is exposed and ready for insertion into a patient. In addition, as the plunger 28 is in the most proximal position, the resilient wire 18 is also fully retracted and disposed inside of the needle 12. The set screw 36 is optionally disposed in the most distal hole 38d (FIG. 5) nearest the hooks 30 of the plunger 28. The plunger 28 may also be designed without the hole 38d such that the first configuration is achieved only so long as a surgeon holds the plunger 28 in the most proximal position. For example, a strong enough spring 24 may be used such that, without the hole or detent 38d, if a surgeon releases the handle 34, the spring 24 automatically transitions the surgical assembly 10 to the second configuration (discussed below), in which the cage 20 is in the lower position and the distal end 14b of the insulating member 14 is disposed beyond the sharp distal end 12b of the needle 12.

If the plunger 28 is manually moved distally from the first configuration, the spring 24, which is compressed, pushes the cage 20 distally toward the lower position, whereby the cage 20 and insulating member 14 are moved by the spring 24 with the movement of the plunger 28. The spring 24 cannot cause a distal displacement of the cage 20 greater than that of the plunger 28 if the plunger 28 is held in place because the rim 32 (FIG. 5) of the cage 20 will be stopped by the hooks 30 of the plunger 20. In other words, if the plunger 28 is stopped after a small distal displacement from the first configuration (e.g. by holding the handle 34 such that the plunger 28 assumes a position where the detents 38*a-d* are not engaged by the ball set screw 36), the cage 20 will come to rest between the upper and lower positions with the spring 24 still in a compressed configuration but unable to push the cage 20 to the lower position on account of the rim 32 of the cage 20 being in contact with the hooks 30 of the plunger 28.

The plunger 28 may be moved distally to arrive at the second configuration (FIGS. 2B, 3B). In the second configuration, the set screw 36 is disposed in the hole 38*c* (FIG. 5), which places the plunger 28 in a first extended position. In this second configuration, the cage 20 is disposed in the lower position, the distal end flange 20*b* of the cage 20 having come up against the horizontal member 22 of the housing 21 as discussed above when the set screw 36 snapped into the hole 38*c* of the plunger 28. Thus, the insulating member 14 travels with the plunger 28 between the first and second configurations, which locates the distal end 14*b* of the insulating member 14 beyond the sharp distal end 12*b* of the needle 12, which protects and insulates the sharp distal end 12. In addition, the cauterizing tip 18*b* of the resilient wire 18, having moved distally as the plunger 28 moved distally, is now disposed beyond the distal end 12*b* of the needle 12, but inside the insulating member 14, which electrically insulates the cauterizing tip 18. This configuration thus allows the surgical assembly 10 to be maneuvered within the patient without cutting any tissue with the sharp distal end 12*b*, and without cauterizing any tissue with the cauterizing tip 18. This second configuration also helps to protect the patient from accidental trauma by blocking the sharp distal end 12*b* of the needle 12. For example, if the needle 12 is inadvertently pushed forward by the surgeon or another person, the insulating member 14 may prevent the surgical assembly 10 from puncturing additional tissue or even a vital organ. As discussed above, a strong enough spring 24 may be utilized to bias the surgical assembly 10 from the first configuration to the second configuration in the event that the plunger 28 is released therebetween. Such an arrangement may increase the safety of the surgical assembly 10 by automatically covering the sharp distal end 12*b* of the needle 12 when the handle 34 is released.

The plunger 28 may be moved distally to arrive at the third configuration (FIGS. 2C, 3C). In the third configuration (FIGS. 2C, 3C), the set screw 36 is disposed in the hole 38*b* (FIG. 5), which places the plunger 28 in a second extension position. In this third configuration, the distal end 14*b* of the insulating member 14 is disposed beyond the sharp distal end 12*b* of the needle 12. In addition, the cauterizing tip 18*b* of the resilient wire 18 is disposed just beyond the distal end 14*b* of the insulating member 14 along or adjacent the longitudinal axis 12*c* of the needle 12 because when the plunger was moved from the second configuration to the third configuration, the resilient wire 18 moved distally while the cage 20 and insulating member 14 remained stationary, the flange 20*b* of the cage 20 being unable to move because of the horizontal member 22 of the housing 21.

The third configuration allows for the electrical activation and operation of the cauterizing tip 18 while insulating the sharp distal end 12*b* of the needle 12. A leaf spring 40 (FIGS. 4 and 8) and banana plug 42 (FIGS. 4 and 6) are provided to the surgical assembly 10 to electrify the cauterizing tip 18*b*. The banana plug 42 is electronically coupled with the leaf spring 40, and is preferably electronically coupled to a foot pedal (not shown), which, when depressed, supplies current to the banana plug 42. The leaf spring 40 is positioned such that a first end 40*a* is movable and biased towards the elongated member 16 while a second leaf spring end (not shown) is fixed to the housing 21 and/or banana plug 42. The first leaf spring end 40*a* of the leaf spring 40 rides along the exterior surface 29 of the outer wall of the plunger 28 when the plunger is disposed in and between the first (FIG. 3A) and second (FIG. 3B) configurations. When the plunger 28 is moved from the second configuration toward the third configuration (FIG. 3C), the first leaf spring end 40*a* rides along a tapered groove 44 (FIG. 3B) cut into the plunger 28, and makes contact with the elongated member 16 when the plunger 28 reaches the third configuration (in which the set screw 36 is disposed in hole 38*b*), at which point the tapered slot extends all the way through the wall of the plunger 28.

When a foot pedal (not shown) is depressed, electrical current travels up through the banana plug 42, through the leaf spring 40, into and down the elongated member 16, into and down the resilient wire 18, to the cauterizing tip 18*b*. The current and voltage difference between the cauterizing tip 18*b* and the ground, which, in the case of monopolar electro-cauterization, is the patient, generates heat in the cauterizing tip 18*b*. As previously discussed, the resilient wire 18 is preferably insulated between the proximal end 18*a* and the cauterizing tip 18*b*, but not at the cauterizing tip 18*b*. The resilient wire 18 thus becomes a cauterization device that may be used to cauterize surgical areas to stop internal bleeding and/or to cut through tissue inside the patient in order to destroy and/or remove it.

The plunger 28 may again be moved distally to arrive at the fourth configuration (FIGS. 2D, 3D). In the fourth configuration, the set screw 36 is disposed in the hole 38*a* (FIG. 5), which places the plunger 28 in a third extension position. In this fourth configuration, the distal end 14*b* of the insulating member 14 is disposed beyond the sharp distal end 12*b* of the needle 12, and the plunger 28 is fully extended, which fully extends the resilient wire 18 and disposes the cauterizing tip 18*b* even further beyond the distal end 14*b* of the insulating member 14. The resilient wire 18 is preferably resiliently biased toward a bent configuration such that the resilient wire 18 bends as it is exposed and is no longer within the needle 12 and/or insulating member 14. As seen in FIGS. 1 and 2D, the bending of the resilient wire 18 situates the cauterizing tip 18*b* at a location offset from the longitudinal axis 12*c* of the needle, and outside the cylindrical projection of the outer wall of the needle 12.

The fourth configuration also allows for the electrical activation and operation of the cauterizing tip 18 while insulating the sharp distal end 12*b* of the needle 12 with the insulating member 14. In this configuration, the distance at which the cauterization tip 18*b* is offset from the longitudinal axis 12*c* of the needle 12 is at least as large as one half of the outer diameter of the needle 12, and preferably at least as large as twice the outer diameter of the needle 12. The positioning of the cauterizing tip 18*b* outside of the peripheral projection of the needle 12 allows for electrical activation and operation of the cauterizing tip 18*b* and increases the reachable area within the patient after the surgical assembly 10 is inserted through a small incision at a specific location.

Preferably, the cauterizing tip 18*b* of the resilient wire 18 is electrified once it extends beyond the distal ends 12*b*, 14*b* of the needle and insulating member 14. At any time, the resilient wire 18 and elongated member 16 may be retracted within the needle 12 by proximally moving the plunger 28 relative to the needle 12. The surgical assembly can then be pulled out of the body, leaving only a small puncture mark which will often heal without a scar.

The surgical assembly 10 can also be moved from the fourth configuration to the third configuration, from the third configuration to the second configuration, and from the second configuration to the first configuration by simply moving the plunger 28 in a proximal direction, which reverses the process described above. When the plunger 28 is moved in a proximal direction from the second configuration to the first configuration, the hooks 30 of the plunger 28 grab onto the upper rim 32 of the cage 20 and pull the cage 20 toward the upper position, which moves the insulating member 14 proximally to expose the sharp distal end 12b of the needle 12.

The four configurations of the surgical assembly 10 may be used during laparoscopic surgery instead of using extra trocars and laparoscopic instruments. In particular, with the insulating member 14, elongated member 16, and resilient wire 18 all disposed inside the needle 12, the needle 12 is used to puncture the skin, and is advanced into the body (e.g., the abdomen). At a desired location (typically under guidance of an already inserted scope), the movement of the needle 12 is stopped. The plunger 28 is then distally advanced relative to the needle 12 until the distal end 14b of the insulating member 14 extends past the sharp distal end 12b of the needle 12. When the plunger 28 reaches the second configuration, the surgical assembly 10 may be left in place while the surgeon operates another tool, as this configuration insulates the needle 12 and acts as a barrier to help prevent injury or trauma to the patient. The plunger 28 may then be further distally advanced to the third and fourth configurations, which extend and expose the resilient wire 18 and enable the surgical assembly 10 to be used as an insulated electro-cauterization tool. It is noted that because of the small diameter of the surgical assembly 10, withdrawal of the needle 12 from the abdomen will not cause desufflation, and should not require stitching to close the wound. It is also noted that because of the small diameter of the surgical assembly 10 and the elimination of a trocar port, the surgical assembly 10 can be easily moved in any direction (i.e., it can be easily angled) during surgery. The surgical assembly 10 of the invention utilizes a minimum number of parts and may be used to replace expensive trocar assemblies and laparoscopic instruments.

It will be appreciated by those skilled in the art that the minimally invasive surgical assembly 10 can be used for various surgical procedures, including but not limited to, tuboplasty, gastric bypass, bowel connection, kidney surgery, appendectomy, menisectomy, discectomy, etc. The minimally invasive surgical assembly 10 of the invention also has particularly advantageous uses in neonatal and pediatric surgeries, and may be used on animals or cadavers.

There have been described and illustrated herein several embodiments of a surgical assembly and methods of its use. While particular embodiments of the invention have been described, it is not intended that the invention be limited thereto, as it is intended that the invention be as broad in scope as the art will allow and that the specification be read likewise. Thus, while particular materials for making the needle, insulating member, elongated member, and resilient member have been disclosed, it will be appreciated that other materials may be used as well. In addition, while particular fixing elements and systems have been disclosed for fixing and moving the insulating member and elongated member relative to needle, it will be understood that other mechanisms can be used. Further, while the needle, insulating member, and elongated member have been shown as being straight, because of their small diameter they may be bent together by the user, or one or both may be formed with a bend (arc). Moreover, while particular configurations have been disclosed in reference to the relative positions of the needle, insulating member, elongated member, and resilient wire relative to each other, it will be appreciated that other configurations could be used as well. In addition, while specific sizes, dimensions, and angles have been disclosed for the surgical assembly and its components, it will be appreciated that other dimensions, sizes, and angles may be used. It will therefore be appreciated by those skilled in the art that yet other modifications could be made to the provided invention without deviating from its spirit and scope as claimed.

The invention claimed is:

1. A surgical instrument assembly comprising:
   a hollow needle having a longitudinal axis, and a sharp distal end;
   an insulating member operably disposed within said hollow needle and being movable relative to said hollow needle, said insulating member having a distal end;
   a wire movable through and relative to both said insulating member and said hollow needle, wherein said wire is retractable within both of said insulating member and said hollow needle and extendable beyond both of said distal end of said insulating member and said sharp distal end of said hollow needle, said wire having a distal tip;
   a housing fixed to said hollow needle;
   a sub-assembly disposed at least partially inside said housing, said sub-assembly being operable to move said insulating member relative to said hollow needle and move said wire relative to said hollow needle and said insulating member, said sub-assembly including a cage and a plunger, said cage being mechanically coupled to said insulating member, and said plunger being mechanically coupled to said wire and movable relative to said cage in a distal direction relative to said hollow needle; and
   a leaf spring configured to selectively be insulated from said wire by the plunger and be placed in electrical contact with said wire such that said wire can be electrified to function as a cautery device, the leaf spring being biased toward contact with the wire,
   wherein said plunger has engaging means for selectively engaging said cage to move said cage proximally along a portion of said longitudinal axis of said hollow needle whereby said insulating member is moved proximally relative to said hollow needle, and
   wherein said plunger defines a plurality of detents or holes to fix said surgical instrument assembly in a plurality of predefined configurations.

2. The surgical instrument assembly according to claim 1, wherein said engaging means comprises projections, hooks, or a flange extending radially relative to said longitudinal axis.

3. The surgical instrument assembly according to claim 1,
   wherein said cage is movable along said longitudinal axis from a lower position to an upper position and vice versa relative to said sharp distal end of said hollow needle,
   wherein said plunger is movable along said longitudinal axis from a proximal position through a decoupling position to a distal position relative to said sharp distal end of said hollow needle,
   wherein, when said plunger is disposed between said proximal position and said decoupling position, said engaging means of said plunger engage said cage, and movement of said plunger causes said insulating member and said wire to move relative to said hollow needle, and wherein, when said plunger is moved between said decoupling position and said distal position, said wire moves relative to said hollow needle while said insulating member is stationary relative to said hollow needle.

4. The surgical instrument assembly according to claim 3, wherein said housing includes a member substantially perpendicular to said longitudinal axis that prevents said cage from moving distally beyond said lower position.

5. The surgical instrument assembly according to claim 3, wherein said plunger and said cage are situated such that said cage is disposed in said upper position when said plunger is disposed in said proximal position, and said cage is disposed in said lower position when said plunger is disposed between said decoupling position and said distal position.

6. The surgical instrument assembly according to claim 3, further comprising:
a spring-loaded set screw mounted to said housing, wherein said spring-loaded set screw is received by at least one of the plurality of detents or holes defined by said plunger to temporarily fix said surgical instrument assembly in at least one of a first, second, third, and fourth configurations of the plurality of predefined configurations.

7. The surgical instrument assembly according to claim 1, wherein said surgical instrument assembly is configured to assume at least a first configuration and a second configuration of the plurality of predefined configurations,
wherein in said first configuration of the plurality of predefined configurations, said wire and said insulating member are disposed inside of said hollow needle such that said sharp distal end of said hollow needle is exposed, and
wherein in said second configuration of the plurality of predefined configurations, said insulating member extends parallel to the longitudinal axis of the hollow needle beyond said sharp distal end of said hollow needle and said wire is completely disposed within said insulating member such that the distal tip of said wire is proximal to said distal end of said insulating member.

8. The surgical instrument assembly according to claim 7, wherein said surgical instrument assembly is further configured to assume a third configuration and a fourth configuration of the plurality of predefined configurations,
wherein in said third configuration of the plurality of predefined configurations, said distal end of said wire extends beyond both said distal end of said insulating member and said sharp distal end of said hollow needle, and said distal end of said insulating member is disposed beyond said sharp distal end of said hollow needle such that said sharp distal end is protected, and
wherein in said fourth configuration of the plurality of predefined configurations, said distal tip of said wire extends beyond both said distal end of said insulating member and said sharp distal end of said hollow needle, said insulating member extends beyond said sharp distal end of said hollow needle in a direction parallel to the longitudinal axis of said hollow needle, and said distal tip of said wire is offset from said longitudinal axis of said hollow needle by a distance greater than one half of an outer diameter of said hollow needle.

9. The surgical instrument assembly according to claim 8, wherein said leaf spring is insulated from said wire when said surgical instrument assembly is placed in said first or second configuration of the plurality of predefined configurations, and
wherein said leaf spring is in electrical contact with said wire when said surgical instrument assembly is placed in said third or fourth configuration of the plurality of predefined configurations.

10. The surgical instrument assembly according to claim 1,
wherein said sub-assembly further includes a spring, said spring having one end fixed to said housing and another movable end in contact with said cage,
wherein said spring biases both said cage and said insulating member in the distal direction relative to said housing.

11. The surgical instrument assembly according to claim 1, further comprising:
an elongated member extending through said hollow needle and connecting to a proximal end of said wire.

12. The surgical instrument assembly according to claim 1, wherein said wire is biased toward a bent configuration whereby said distal tip moves away from said longitudinal axis of said hollow needle when said distal tip extends beyond said distal end of said insulating member.

13. The surgical instrument assembly according to claim 1, wherein the outer diameter of said hollow needle is 2.2 mm±20%.

14. A surgical instrument assembly comprising:
a hollow needle having a longitudinal axis, and a sharp distal end;
an insulating member operably disposed within said hollow needle and being movable relative to said hollow needle, said insulating member having a distal end;
a wire movable through and relative to both said insulating member and said hollow needle, wherein said wire is retractable within both of said insulating member and said hollow needle and extendable beyond both of said distal end of said insulating member and said sharp distal end of said hollow needle, said wire having a distal tip;
a housing fixed to said hollow needle; and
a sub-assembly disposed at least partially inside said housing, said sub-assembly being operable to move said insulating member relative to said hollow needle and move said wire relative to said hollow needle and said insulating member, said sub-assembly including a cage, a spring, and a plunger, said cage being mechanically coupled to said insulating member, said spring having one end fixed to said housing and another movable end in contact with said cage, and said plunger being mechanically coupled to said wire and movable relative to said cage in a distal direction relative to said hollow needle; and
a leaf spring configured to selectively be insulated from said wire by the plunger and be placed in electrical contact with said wire such that said wire can be electrified to function as a cautery device, the leaf spring being biased toward contact with the wire,
wherein said spring biases both said cage and said insulating member in the distal direction relative to said housing,
wherein said plunger having engaging means for selectively engaging said cage to move said cage proximally along a portion of said longitudinal axis of said hollow needle whereby said insulating member is moved proximally relative to said hollow needle, wherein said plunger defines a plurality of detents or holes to fix said surgical instrument assembly in a plurality of predefined configurations.

15. The surgical instrument assembly according to claim 14,
wherein said surgical instrument assembly is configured to assume at least a first configuration and a second configuration of the plurality of predefined configurations,
wherein in said first configuration of the plurality of predefined configurations, said wire and said insulating member are disposed inside of said hollow needle such that said sharp distal end of said hollow needle is exposed, and
wherein in said second configuration of the plurality of predefined configurations, said insulating member extends parallel to the longitudinal axis of the hollow needle beyond said sharp distal end of said hollow needle and said wire is completely disposed within said insulating member such that the distal tip of said wire is proximal to said distal end of said insulating member.

16. The surgical instrument assembly according to claim 15,
wherein said surgical instrument assembly is further configured to assume a third configuration and a fourth configuration of the plurality of predefined configurations,
wherein in said third configuration of the plurality of predefined configurations, said distal tip of said wire extends beyond both said distal end of said insulating member and said sharp distal end of said hollow needle, and said distal end of said insulating member is disposed beyond said sharp distal end of said hollow needle such that said sharp distal end is protected, and
wherein in said fourth configuration of the plurality of predefined configurations, said sharp distal tip of said wire extends beyond both said distal end of said insulating member and said sharp distal end of said hollow needle, said insulating member extends beyond said sharp distal end of said hollow needle in a direction parallel to the longitudinal axis of said hollow needle, and said distal tip of said wire is offset from said longitudinal axis of said hollow needle by a distance greater than one half of an outer diameter of said hollow needle.

17. The surgical instrument assembly according to claim 14, further comprising:
an elongated member extending through said hollow needle and connecting to a proximal end of said wire.

18. The surgical instrument assembly according to claim 14, wherein said wire is biased toward a bent configuration whereby said distal tip moves away from said longitudinal axis of said hollow needle when said distal tip extends beyond said distal end of said insulating member.

19. The surgical instrument assembly according to claim 14, wherein an outer diameter of said hollow needle is 2.2 mm±20%.

* * * * *